United States Patent [19]
Carroll et al.

[11] Patent Number: 5,974,886
[45] Date of Patent: Nov. 2, 1999

[54] METHOD AND APPARATUS FOR THICKNESS DETERMINATION IN MULTILAYER ARTICLES

[75] Inventors: James Jorgly Carroll, Ballston Lake; John Broddus Deaton, Jr.; Ram Kumar Upadhyay, both of Niskayuna; Robert Snee Gilmore, Burnt Hills, all of N.Y.; Robert Stanley Thayer, Pittsfield, Mass.

[73] Assignee: General Electric Company, Schenectady, N.Y.

[21] Appl. No.: 08/937,264

[22] Filed: Sep. 15, 1997

[51] Int. Cl.$^6$ ..................................................... G01N 29/10
[52] U.S. Cl. ................. 73/598; 73/602; 73/622; 73/629; 73/1.82
[58] Field of Search ............................. 73/597, 598, 599, 73/600, 602, 620, 622, 623, 627, 629, 631, 1.82, 1.86, 617, 644

[56] References Cited

U.S. PATENT DOCUMENTS

| | | |
|---|---|---|
| 3,688,565 | 9/1972 | Brech . |
| 4,100,808 | 7/1978 | Evans et al. ............................... 73/588 |
| 4,512,194 | 4/1985 | Beuter ....................................... 73/579 |
| 4,625,556 | 12/1986 | Sukahara et al. .......................... 73/602 |
| 5,038,615 | 8/1991 | Trulson et al. ............................ 73/597 |
| 5,408,881 | 4/1995 | Piché et al. ................................ 73/582 |
| 5,608,165 | 3/1997 | Mozurkewich, Jr. ...................... 73/599 |
| 5,661,241 | 8/1997 | Harth, III et al. ......................... 73/622 |
| 5,663,502 | 9/1997 | Nagashima et al. ...................... 73/599 |

*Primary Examiner*—Michael Brock
*Assistant Examiner*—Rose M. Miller
*Attorney, Agent, or Firm*—Patrick K. Patnode; Marvin Snyder

[57] ABSTRACT

An exemplary apparatus for determining the thicknesses of individual layers in a multilayer article comprises an ultrasonic transducer coupled to the multilayer article with a buffer rod of similar acoustic properties, a pulser-receiver-amplifier which generates ultrasonic waves to produce discernible, time resolved pulse echoes, a digitizing oscilloscope which may be used to view the received pulse echoes, and a computer for controlling data acquisition and analysis. The computer is programmed to execute the exemplary method, which comprises the steps of selecting a center frequency of a transducer such that respective pulse echoes produced at the interfaces between layers of the multilayer article each have a common distinguishing feature with a signal to noise ratio greater than or equal to a predetermined value, and the pulse echoes are resolved in time; determining a transit time correction factor for the layer of the multilayer article based on an actual transit time measured with the transducer adjacent to the layer and an apparent transit time measured with the transducer not adjacent to the layer; propagating a pulse through the multilayer article to produce pulse echoes at the interfaces between the layers of the multilayer article; determining a measured transit time of the pulse through the layer based on the pulse echoes at the interfaces of the layer; and calculating a thickness of the layer based on the measured transit time and the transit time correction factor.

6 Claims, 3 Drawing Sheets

5,974,886

METHOD AND APPARATUS FOR THICKNESS DETERMINATION IN MULTILAYER ARTICLES

BACKGROUND

1. Field of the Invention

The present invention relates generally to ultrasonic thickness determination, and more particularly to a method and apparatus for nondestructively determining the thickness of individual layers in multilayer articles.

2. Description of the Related Art

The determination of thickness by propagation of ultrasonic waves through an article is well known in the art. Typically, a transducer is used to generate an ultrasonic pulse which propagates through the article and is reflected off an acoustic interface and received by a receiving transducer. By knowing the velocity of the pulse through the article and the time of flight of the pulse, the thickness can be easily determined.

In many engineering applications, it is important to be able to monitor the thickness of individual layers in multilayer articles. For example, in the automotive industry, body panels and bumpers are commonly made from multilayer sheets which are extruded and subsequently thermoformed into a final shape. The top and bottom cap layers may comprise a pure LEXAN polycarbonate, for example, which produces a fine cosmetic finish, while the middle layer may comprise LEXAN reinforced with glass fibers for strength. During the thermoforming process, the multilayer sheets are typically stretched in a non-uniform manner, with some local areas experiencing a large degree of strain. If a cap layer is initially too thin, it may be strained to such a degree in some areas during thermoforming that cosmetic defects result, such as blistering or delamination. The ability to monitor and control the thickness of individual layers during the extrusion and thermoforming processes can thus be very important in avoiding cosmetic defects which can occur if the layer thicknesses deviate beyond specified tolerances.

Systems are known for ultrasonically monitoring layer thicknesses in certain multilayer articles. For example, U.S. Pat. No. 5,038,615 to Trulson et al. discloses a method for measuring the thickness of individual paint layers on a substrate. The Trulson method involves propagating ultrasonic waves through the object, averaging several pulse echoes indicative of each layer interface, and comparing the averaged waveform to a stored reference waveform.

The Trulson method, however, has limited applicability. For example, the Trulson method is designed to operate with layers, such as paint layers, which have very distinct interfaces, so that the pulse echoes correspond well with the stored reference waveform. However, in applications in which the interfaces between layers are indistinct and variable, the resulting pulse echoes have an uncertain shape, phase, and amplitude. In such applications, the Trulson method can not reliably correlate the pulse echoes with a reference waveform. The Trulson method also does not take into account the effects of attenuation of high frequencies of the pulse bandwidth, which can introduce significant measurement errors.

It would be desirable, therefore, to have a method and apparatus capable of determining the thicknesses of individual layers in a multilayer article in which the interfaces between the layers are unpredictable and indistinct, and where the layers may significantly attenuate the high frequencies of the pulse bandwidth.

SUMMARY

An exemplary apparatus for determining the thicknesses of individual layers in a multilayer article comprises an ultrasonic transducer coupled to the multilayer article with a buffer rod of similar acoustic properties, a pulser-receiver-amplifier which generates ultrasonic waves to produce discernible, time resolved pulse echoes, a digitizing oscilloscope which may be used to view the received pulse echoes, and a computer for controlling data acquisition and analysis.

The computer is programmed to execute the exemplary method, which comprises the steps of selecting a center frequency of a transducer such that respective pulse echoes produced at the interfaces between layers of the multilayer article each have a common distinguishing feature with a signal to noise ratio greater than or equal to a predetermined value, and the pulse echoes are resolved in time; determining a transit time correction factor for the layer of the multilayer article based on an actual transit time measured with the transducer adjacent to the layer and an apparent transit time measured with the transducer not adjacent to the layer; propagating a pulse through the multilayer article to produce pulse echoes at the interfaces between the layers of the multilayer article; determining a measured transit time of the pulse through the layer based on the pulse echoes at the interfaces of the layer; and calculating a thickness of the layer based on the measured transit time and the transit time correction factor.

The method and apparatus, according to exemplary embodiments of the invention, can accurately determine the thicknesses of individual layers in a multilayer article in which the interfaces between the layers are unpredictable and indistinct, and where the layers may selectively attenuate the high frequencies of the pulse bandwidth.

BRIEF DESCRIPTION OF THE DRAWINGS

Other features and advantages of the invention will be more readily understood upon reading the following detailed description, taken in conjunction with the drawings, in which.

DETAILED DESCRIPTION OF THE PREFERRED EMBODIMENTS

Figure 1:
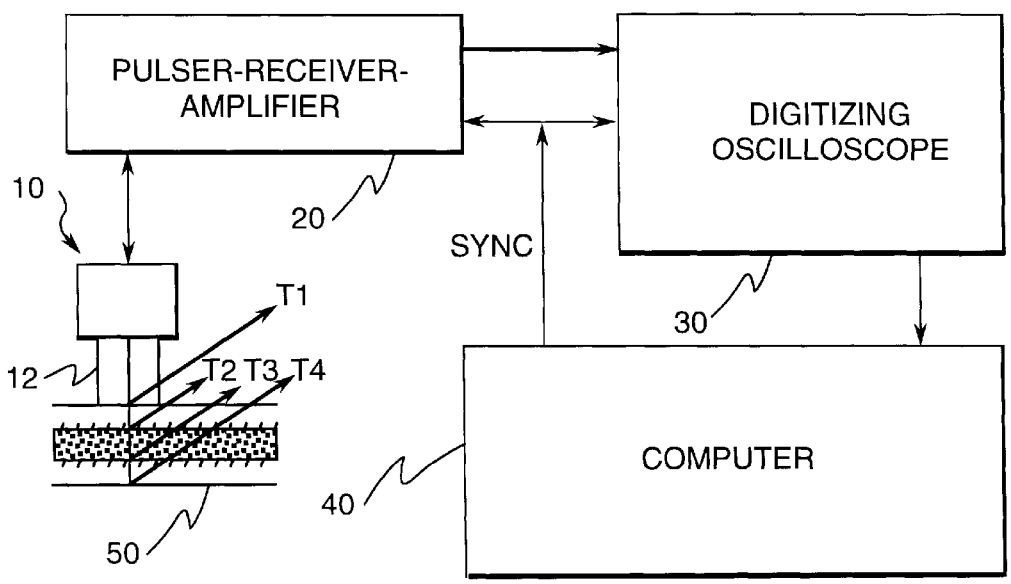
FIG. 1 illustrates a thickness measurement apparatus according to an exemplary embodiment of the invention.

FIG. 1 illustrates a thickness measurement apparatus according to an exemplary embodiment of the invention. As shown in FIG. 1, the apparatus includes a transducer 10, an ultrasonic pulser-receiver-amplifier 20, a digitizing oscilloscope 30, and a computer 40. The transducer 10 typically is a broadband ultrasonic transducer comprising a piezoelectric element which generates an ultrasonic pulse in response to an applied voltage. A buffer rod 12 couples the ultrasonic pulse into the article 50 under inspection. A liquid couplant may be provided between the buffer rod 12 and the article 50 to reduce the energy reflected at the surface of the article 50.

The ultrasonic pulser-receiver-amplifier 20 generates an electrical signal to activate the transducer 10, receives signals generated by the transducer 10 representing pulse echoes, and amplifies the received signals. The amplified signals are transmitted to a digitizing oscilloscope 30. Alternately, an analog-to-digital conversion board can be provided in the computer 40 in lieu of the digitizing oscilloscope 30. The digitizing oscilloscope 30 displays the received signals for an operator to view. The digitized signals are also transmitted to the computer 40 for processing.

The computer 40, which may be portable, is typically used for data acquisition, data analysis, system control, and data storage. For example, the computer 40 may be programmed to synchronize the pulse repetition rate for the ultrasonic signals, provide instructions for data transfer from the digitizing oscilloscope 30, set operating parameters for the ultrasonic pulser-receiver-amplifier 20, analyze the data, store the data, and tabulate the data. The computer is suitably programmed to carry out the method according to exemplary embodiments of the invention, which will be described further below. The computer 40 may be an IBM-compatible personal computer with an IEEE interface, for example.

Figure 2:
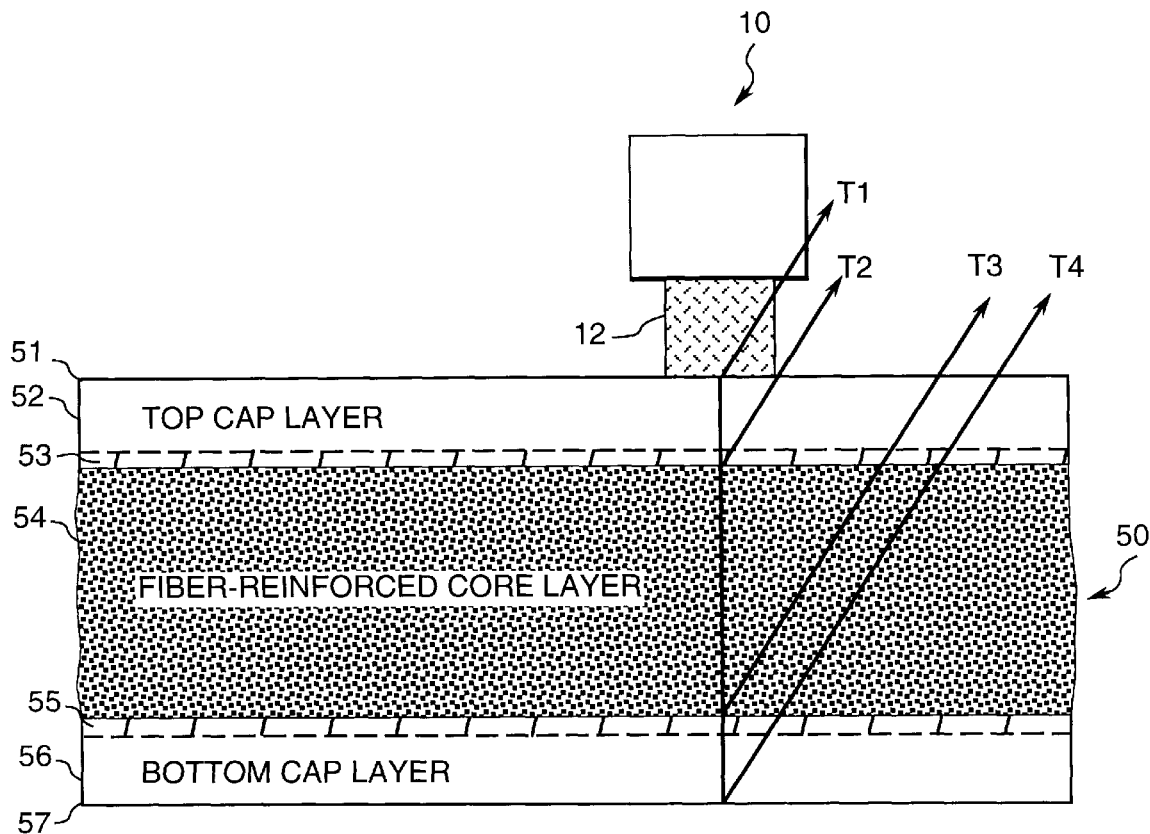
FIG. 2 illustrates a multilayer article having relatively indistinct layer interfaces.

FIG. 2 illustrates an example of a multilayer article 50 having layers which can be measured with exemplary embodiments of the invention. In general, the interfaces between the layers reflect at least a small percentage of the ultrasonic energy incident upon them. The reflections can result from differences in the acoustic properties of the materials forming the interface, as shown in FIG. 2, or from a property of the interface itself, such a common grain boundary formed in a diffusion bond of two statistically alike materials.

In FIG. 2, the exemplary multilayer article 50 comprises a top cap layer 52 of pure LEXAN, a core layer 54 of LEXAN reinforced with glass fibers, and a bottom cap layer 56 also of pure LEXAN. Such a multilayer structure is commonly used for body panels and bumpers in the automotive industry. The top and bottom cap layers 52, 56 provide a smooth cosmetic finish, while the core layer provides strength to the structure.

The three layer structure 50 shown in FIG. 2 is typically formed in a sheet extrusion process. In sheet extrusion, the individual layers are extruded through respective dies and subsequently joined together with a roller. During this process, the thicknesses of individual layers may deviate from desired tolerances, although the total thickness of the article 50 may remain relatively constant. Therefore, it is desirable to monitor the thicknesses of individual layers as well as the total thickness.

Figure 4:
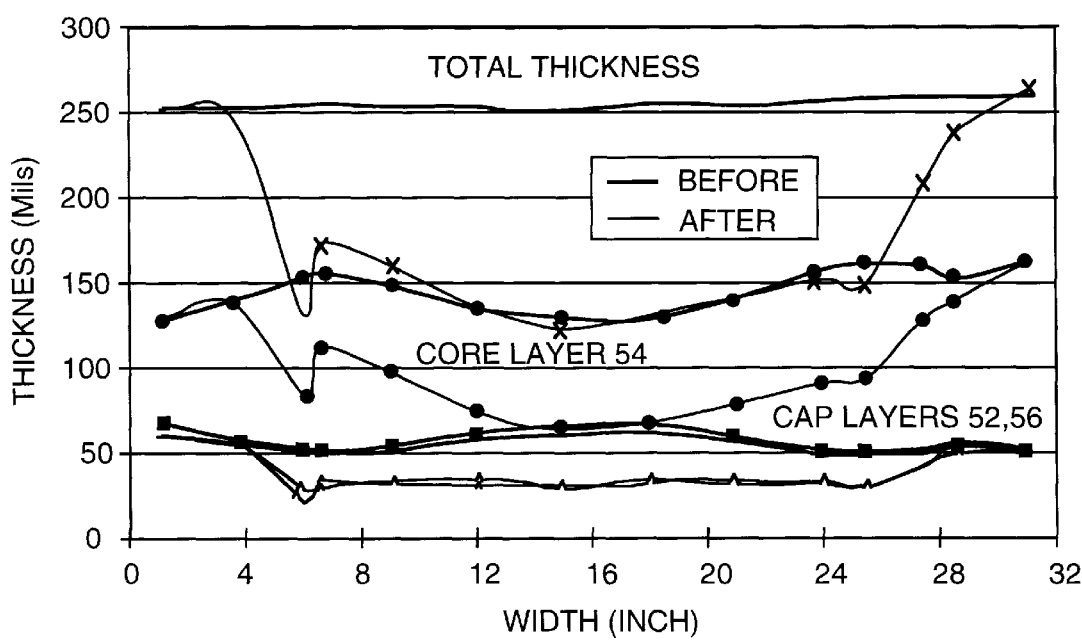
FIG. 4 illustrates layer thicknesses of a multilayer article before and after a thermoforming process has taken place on the article.

After the multilayer article 50 has been formed by extrusion, it can be thermoformed into its final shape. The thermoforming process involves shaping the heated article in a mold, during which the thickness of individual layers may change substantially. This change is illustrated in FIG. 4, in which the dark lines show the thickness of each layer before thermoforming, and the thin lines show the layer thicknesses after thermoforming. To ensure that the final product has an acceptable appearance, it is desirable to maintain the initial thickness of individual layers within certain tolerances. The thickness measurement system, according to exemplary embodiments of the invention, can be used during both the sheet extrusion process and the thermoforming process to monitor layer thickness, and the resulting data can be used to optimize and control the manufacturing processes.

Measurement of the thicknesses of the layers 52, 54, 56 of the article 50 can be complicated by several factors. For example, as a result of the extrusion and thermoforming processes, the interfaces 53 and 55 between the cap layers 52, 56 and the core layer 54, are typically diffuse in nature. The interfaces 53 and 55 have a finite thickness, as the material changes from pure LEXAN to LEXAN reinforced with glass, for example. The interfaces 53 and 55 thus typically have a composition gradient which results in a gradual transition in acoustic properties from one layer to the next. In addition, the interfaces 53 and 55 are not always flat, which may cause a diversion of energy away from the receiving transducer. These factors typically cause the interfaces 53, 55 to have a very low ultrasonic reflectivity, and the resulting pulse echoes to have a low amplitude, uncertain phase, and uncertain shape.

Figure 3:
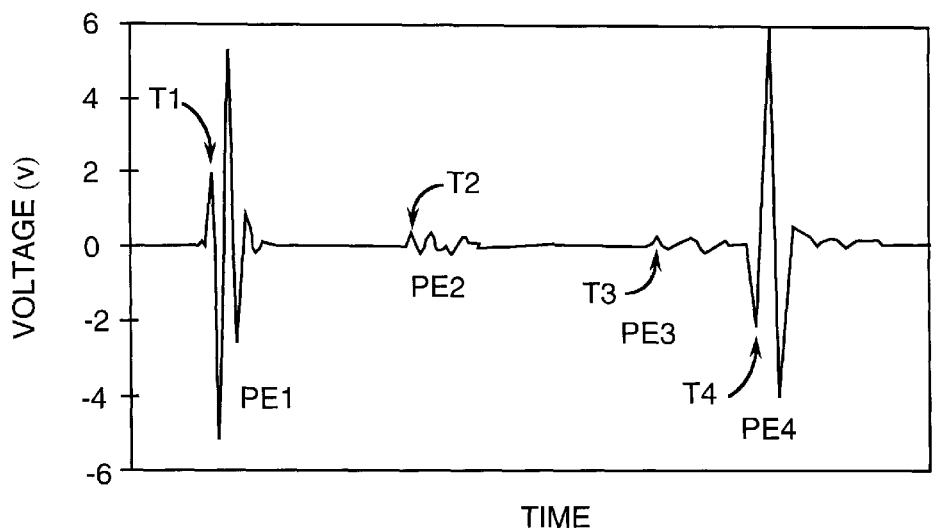
FIG. 3 illustrates a received signal containing four pulse echoes according to an exemplary embodiment of the invention.

The result of these factors is exhibited in the pulse echoes which are reflected off the interfaces 53 and 55. FIG. 3 illustrates a typical signal received by the ultrasonic pulser-receiver-amplifier 20, which includes four pulse echoes PE1–PE4 reflected from the top surface 51, interface 53, interface 55, and bottom surface 57 of the article 50, respectively. As can be seen from FIG. 3, there is typically a substantial difference between the amplitudes of the outer pulse echoes PE1, PE4 and the amplitudes of the inner pulse echoes PE2, PE3. A significant amount of the pulse energy is reflected at the top and bottom surfaces 51, 57 of the article 50, whereas a much smaller amount of energy is reflected at the indistinct interfaces 53, 55 between the cap layers 52, 56 and the core layer 54. The amplitude of the inner pulse echoes PE2, PE3 may be about 5% of the amplitude of the outer pulse echoes PE1, PE4, for example. FIG. 3 also illustrates that the phase and shape of the inner pulse echoes PE2, PE3 can be unpredictable.

Figure 5:
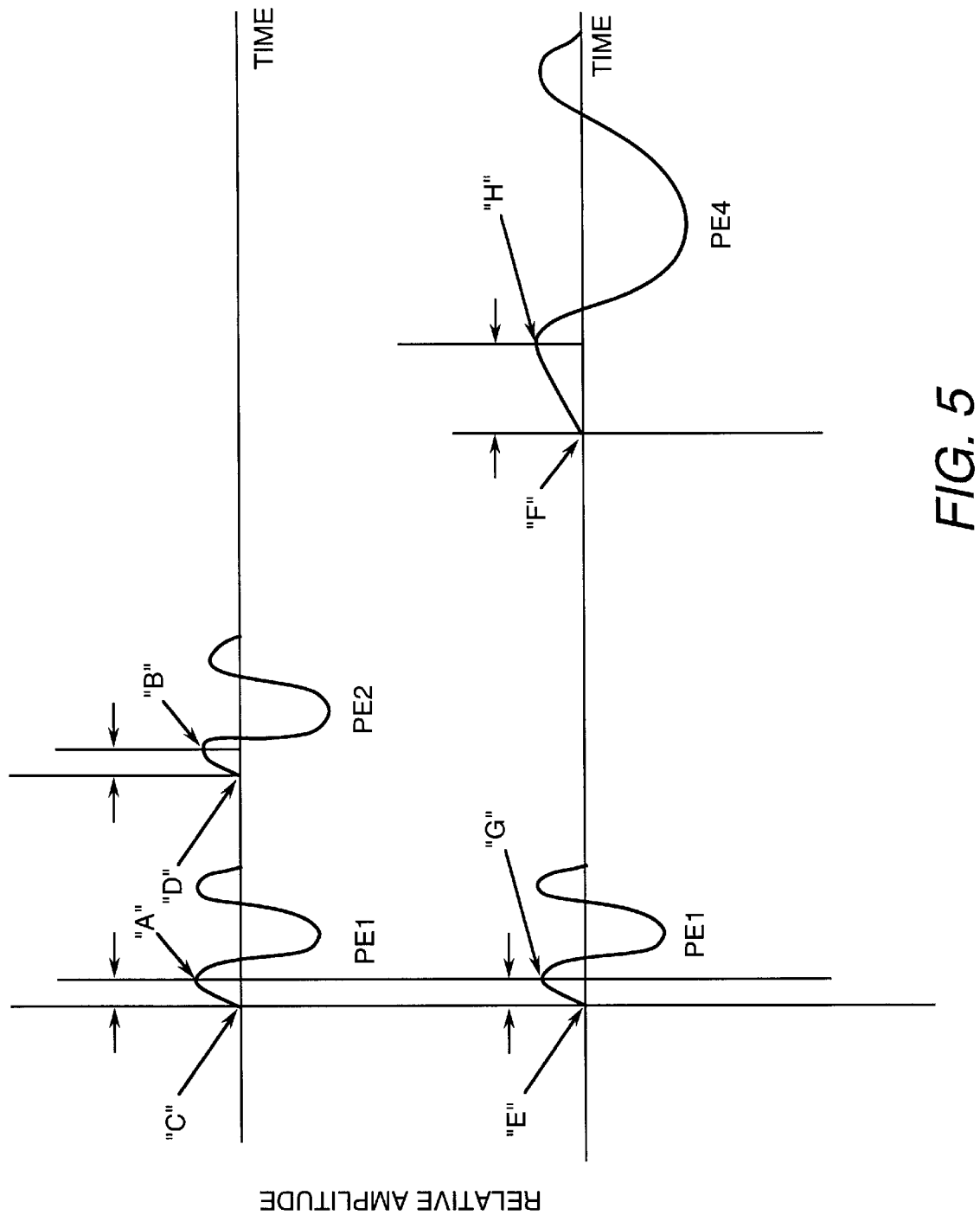
FIG. 5 illustrates the effect of selective frequency attenuation on an ultrasonic pulse.

In addition, many materials, such as LEXAN, selectively attenuate the higher frequencies of the pulse bandwidth, which shifts the center frequency of the pulse to a lower value. For example, a pulse initially having a center frequency of 5 MHz may, after propagation through the article 50, have a center frequency of about 2.5 MHz. This effect is illustrated in FIG. 5, which shows the behavior of a pulse as it propagates through an article comprising a frequency attenuating material such as LEXAN. Initially, the pulse has a preselected center frequency. As illustrated in the top line of FIG. 5, after propagation through only a small portion of the article (e.g. the top cap layer 52 in FIG. 2), the pulse echo PE2 has substantially the same center frequency as the pulse echo PE1 produced at the surface of the article 50, because selective frequency attenuation is relatively insignificant through the top cap layer 52. However, as shown in the bottom line of FIG. 5, after the pulse has propagated further (e.g. to the bottom surface 57), the center frequency in the pulse echo PE4 produced by the bottom interface 57 of the article 50 is significantly lower, due to selective attenuation of the high frequencies of the pulse during propagation.

The reduction in center frequency can introduce substantial measurement errors depending on how the pulse is used to determine transit times. For example, in the upper horizontal axis of FIG. 5, where attenuation of the higher frequencies is insignificant because of the relatively short propagation distance, the time between the leading edges (points "C" and "D") of the pulse echoes PE1 and PE2 is substantially the same as the time between the initial peaks "A" and "B" which are typically used as reference time points. In the lower horizontal axis of FIG. 5, the pulse has traveled over a substantially greater distance through the entire article 50, and selective attenuation of the higher frequencies has reduced the center frequency of the pulse, as shown in PE4. The time between the first peaks "G" and "H" which are typically used as reference time points is significantly longer than the time between the points "E" and "F" which represent the leading edges of the respective pulse echoes. This time difference is a source of error which is compensated according to exemplary embodiments of the invention.

The method and apparatus according to exemplary embodiments of the invention reliably measure layer thickness in multilayer articles which comprise frequency attenuating materials and which have indistinct layer interfaces, such as those shown in FIG. 2. The measurements are accomplished by selecting the transducer operating parameters to yield discernible pulse echoes, while compensating the measurements to correct for errors arising from physical phenomena occurring during propagation such as selective frequency attenuation of the higher frequencies of the pulse bandwidth.

The center frequency of the transducer 10 is typically selected to satisfy two considerations. First, the center frequency of the transducer has a value which is high enough that the resulting pulse echoes PE1–PE4 are resolved in time, i.e. do not overlap in time. The width of the pulse, which typically corresponds to 3/2 of the carrier wavelength, is thus less than the time period between any of the pulse echoes.

Second, the center frequency of the transducer is sufficiently low to minimize excessive attenuation in amplitude by materials, such as LEXAN, through which the pulse is propagated. The carrier frequency has a value which is low enough to allow the amplitudes of the pulse echoes PE2, PE3 to remain large enough to be detected over background noise. For example, the center frequency of the transducer 10 is typically selected to be low enough so that each pulse echo PE1–PE4 has a common distinguishing feature, e.g. the first significant half wave, with a signal to noise ratio of at least 2. This is illustrated in FIG. 3, in which the peak of the first significant half wave of each pulse echo, designated by T1, T2, T3, T4, has a signal to noise ratio of at least 2.

For an article 50 having a total thickness of ½ inch, the transducer center frequency is between 2.25 and 3.5 MHz, according to one exemplary embodiment. When the total thickness of the article is ¼ inch and ⅛ inch, respectively, the transducer frequency is typically about 3.5 MHz and 5–7 MHz. The bandwidth of the transducer is typically about 70–90% of the center frequency.

Other techniques can be implemented to achieve the condition of having a common distinguishing feature on each pulse echo with a signal to noise ratio of greater than 2. For example, the amplitudes of the inner pulse echoes PE2 and PE3 can be increased by reducing the amplitude of the ultrasound reflected at the surface 51 of the article 50 and therefore increasing the amplitude of the ultrasound transmitted to interfaces 53, 55. This may be accomplished by providing a buffer rod 12 and a liquid couplant which have acoustic properties similar to those of the article 50. For example, for a plastic article, the buffer rod 12 typically comprises polystyrene, and the couplant comprises glycerin. For a metallic article 50, an aluminum buffer rod 12 and a gallium couplant may be used. Preferably, the length of the buffer rod 12 is at least as great as the thickness of the article 50 to prevent interference of the second buffer rod echo with the pulse echoes PE1–PE4 from the article being measured.

Also, the power and damping of the pulser-receiver-amplifier driving the transducer 10 can be adjusted to achieve the condition that each pulse echo has a common distinguishing feature with a signal to noise ratio of at least 2. For example, the power of the pulser-receiver-amplifier 20 may be increased to increase the amplitudes of the pulse echoes PE2 and PE3 relative to the noise level. The damping may be increased accordingly to maintain the time resolution of each pulse echo. This principle may be applied individually to each pulse echo. For example, a first power level may be selected for measurement of the pulse echoes PE1 and PE4 with a first pulse, and a second, higher power level may be selected for measurement of the lower amplitude pulse echoes PE2 and PE3 with a second pulse. Such a dual power level may be beneficial when the power level which produces discernible (e.g. signal to noise ratio >2) pulse echoes PE2, PE3 is high enough to produce clipping of the pulse echoes PE1, PE4.

Another feature of the measurement method according to exemplary embodiments of the invention involves a compensation for disturbances in the pulse which occur during propagation through the multilayer article 50, such as a reduction in the center frequency of the pulse due to selective frequency attenuation. Another effect which may be compensated for involves the temporal variation in a pulse echo which may be caused by the finite depth of the interfaces 53, 55 which results from a composition gradient at the interfaces. The compensation, according to one embodiment, involves obtaining three measurements as follows.

In the first step of the compensation, the velocity of a pulse propagating through an isolated test sample of known thickness of the material of the first layer 52 is obtained by measuring the travel time between the pulse echoes from the front and back surfaces of the test sample. The travel time between the pulse echoes is preferably measured between reference time points on a common distinguishing feature of the two pulse echoes. For example, points "A" and "B" in FIG. 5 can be used, which are the maximum points of the first significant half wave of each pulse, and represent points of consistent phase.

In step two of the compensation, the transducer 10 is placed on a first side of the multilayer article 50, as shown in FIG. 2, to generate a pulse and detect a received signal. Assuming that the velocity of the pulse through the first layer 52 adjacent to the transducer 10 is the same as the velocity measured on the test sample in step one, and that the center frequency of the pulse has not changed significantly, the thickness of the first layer 52 can be determined by the travel time of the pulse echo.

The travel time of the pulse through the first layer 52 is measured between reference time points of a common distinguishing feature of the pulse echoes PE1 and PE2. For example, as shown in FIG. 3, the transit time of the pulse through the first layer 52 is measured between points T1 and T2, which are both local maxima of consistent phase of the first significant half wave on their respective pulse echoes PE1 and PE2. The velocity of step 1 multiplied by the travel time measured in this manner (and divided by 2 to account for the round trip) gives an accurate determination of the thickness of the top cap layer 52.

The third step in the compensation involves placing the transducer 10 on the opposite surface 57 of the article 50 adjacent to the bottom layer 56, generating a pulse, and detecting a received signal. For the bottom layer 56 adjacent to the transducer, the transit time through the bottom layer yields an accurate determination of the thickness of the bottom layer 56, assuming the velocity is the same as that measured in step 1 with the test sample and that selective frequency attenuation in the bottom layer 56 is insignificant. Since the thicknesses of the top and bottom cap layers 52, 56 are known, and the total thickness of the article 50 can be easily measured, the thickness of the middle layer 54 can be determined accurately by subtraction.

The next step involves compensation for frequency attenuation and other perturbations by calculating a transit time correction factor $C_{tt}$ for each layer of the multilayer article 50. Qualitatively, the transit time correction factor $C_{tt}$ is used to adjust the measured transit time to yield an accurate measurement of thickness, when the measured transit time includes errors such as from selective frequency attenuation. For example, the transit time through the top layer 52 of a pulse transmitted from the bottom surface 57 appears to be longer than the transit time measured when the transducer is on the top surface 51, due to a reduction in the center frequency of the pulse echo, as shown in FIG. 5. Thus, a transit time correction factor $C_{tt}$ may be calculated for measurement of the top cap layer 52 from the bottom surface 57 as follows:

$$C_{tt} = T_{ac}/T_{ap}$$

where $T_{ac}$ is the actual transit time for the top cap layer 52 measured in step 2 above, and $T_{ap}$ is the "apparent" transit time for the top cap layer 52 measured from the opposite side (bottom 57) of the article in step 3 above.

The correct thickness of the top cap layer 52 can then be determined with a subsequent opposite side (57) transit time measurement $T_{meas}$ by using an adjusted transit time $T_{adj}$ which compensates the opposite side transit time measurement $T_{meas}$ for errors resulting from, for example, a reduction in the center frequency of the pulse. The adjusted transit time is calculated by:

$$T_{adj} = (T_{meas})(C_{tt})$$

The correct thickness is calculated as follows:

$$\text{Thickness} = V(T_{adj})/2$$

where V is the ultrasonic velocity in the top cap layer 52.

This procedure can be repeated to obtain a transit time correction factor $C_{tt}$ for any layer with respect to a measurement made at either or both the top and bottom surfaces 51, 57. For example, a transit time correction factor $C_{tt}$ can be calculated for the middle layer 52 with respect to a measurement made by the transducer 10 from the upper surface 51. The transit time correction factors for each layer can be stored in the computer 40 to be applied to subsequent measurements to obtain accurate values of the thicknesses of individual layers, even when the measurements are conducted from only one side of the article. Typically, it is not necessary to calculate a transit time correction factor $C_{tt}$ for the layer adjacent to the transducer, since it is assumed that the pulse has not traveled through the article enough to introduce errors such as those from selective frequency attenuation. This exemplary method of compensation can be executed easily "in the field", if the velocity through one of the cap layers 52, 56 alone can be measured, for example with an isolated test sample of the cap layer material.

The computer 40 can be suitably programmed to instruct the operator to perform the compensation routine to determine the transit time correction factors $C_{tt}$. For example, the computer 40 can be programmed to instruct the user to: input a measured thickness of the isolated test sample, propagate a pulse through the isolated test sample to obtain a travel time measurement and a velocity, input a measured total thickness of the multilayer article 50, and propagate a pulse through the multilayer article from first and second sides of the multilayer article 50 to calculate transit time correction factors.

The determination of transit time correction factors $C_{tt}$ provides the advantage that the thicknesses of individual layers in a multilayer article 50 can be accurately determined based on measurements from only one side of the article 50. This capability is very useful in applications in which only one side of the article 50 is accessible to the transducer.

After the transit time correction factors $C_{tt}$ have been calculated to account for selective frequency attenuation and other effects of propagation such as a temporal shift in a pulse due to the depth of the interface 53, 55, testing begins by activating the transducer 10 with the ultrasonic pulser-receiver-amplifier 20 to generate a pulse which propagates through the article 50 and is reflected off the interfaces 51, 53, 55, and 57, to produce a received signal, such as that shown in FIG. 3.

A noise level value is then calculated from the received signal. This may be accomplished, for example, by digitizing the received signal in the digitizing oscilloscope 30, determining the standard deviation of the points in a sample of the received signal which does not include a pulse echo, and multiplying the standard deviation by 3. The sample used to calculate the noise level value is typically defined for a time interval which is about equal to the length of the interrogating pulse.

Next, a distinguishing feature of each pulse echo is identified to obtain a reference time point (e.g. T1, T2, T3, T4) for each pulse echo. Preferably, the signal to noise ratio of the distinguishing feature of each pulse echo is at least 2.0. According to one embodiment, the maxima of the first significant half wave of each pulse echo are identified, wherein these maxima each have signal to noise ratios of at least 2.0. Preferably, the reference time points for each of the pulse echoes PE1 and PE4 are selected using a common distinguishing feature, e.g., the peak of the first significant half wave of each pulse echo.

Other distinguishing features which may be used with exemplary embodiments of the invention include: a minimum point of the first significant half wave, maxima and minima of other regions of the pulse echo, zero crossing points, the leading edge of the pulse, and the trailing edge of the pulse. Typically, the maxima and minima are more easily identified than zero crossing points or leading and trailing edges, which may be obscured by noise. When the signal to noise ratio of the common distinguishing feature of each pulse is greater than about 2, the reference time points T1–T4 can be obtained.

The distinguishing feature may be identified visually by an operator as it is displayed on the oscilloscope 30, according to one embodiment. The visual display of the received signal is advantageous, because it allows the operator to dynamically select a common distinguishing feature of a set of pulse echoes which typically have varying and unpredictable shapes. According to this embodiment, the operator marks the reference time points T1–T4 for each pulse echo by positioning a cursor on each common distinguishing feature and clicking a mouse, for example. The computer 40 then derives a value for each reference time point T1–T4 for each pulse echo which is used to determine the thicknesses of each layer. Preferably, the common distinguishing feature used in measuring thicknesses is the same as the common distinguishing feature used in calculating the transit time correction factors $C_{tt}$.

According to another embodiment of the invention, the identification of the reference time points T1–T4 is automated. In this case, the reflected signal is digitized by the oscilloscope 30 and transmitted to the computer 40 which identifies the distinguishing feature according to a programmed method. For example, the computer 40 can be programmed to find a local minimum or maximum having a signal to noise ratio of greater than about 2.0 for each pulse echo, which constitutes the common distinguishing feature. More sophisticated algorithms can be implemented to find other distinguishing features. For example, the computer can be programmed to identify the leading edge of each pulse echo by identifying the peak of the first significant half wave, calculating the center frequency of the pulse echo based on the period of the digitized pulse echo signal, and subtracting a quarter period from the time of the peak of the first significant half wave. The use of the leading edge of each pulse echo as the reference time point would eliminate the error arising from a reduction in the center frequency of the pulse. This procedure can of course be used to find a zero crossing point or the trailing edge of the pulse. The computer 40 can also be programmed to alert the user in the case that the signal to noise ratio for the common distinguishing feature of each pulse echo is less than 2.0.

After the reference time points T1–T4 have been determined for each pulse echo, the travel times between the reference time points are obtained by subtraction. The measured travel times are then multiplied by the appropriate transit time correction factors $C_{tt}$ to obtain adjusted transit times $T_{adj}$ which are in turn used to obtain an accurate determination of the thickness of each layer in the multilayer article 50. Exemplary embodiments of the invention thus provide a system and method which can accurately determine the thicknesses of individual layers in a multilayer article, despite the interfaces between the layers being relatively indistinct. The method and apparatus can also be implemented to make these measurements from only one side of the article, because the physical effects of propagation, such as selective attenuation of the high frequencies of the pulse, or temporal shifts in the pulse echoes due to the depth of the interfaces, are taken into account with the above described compensation method.

Although the invention has been described with regard to particular embodiments, those skilled in the art will recognize that various changes may be made without departing from the scope and spirit of the invention as defined in the following claims. For example, other types of metal and plastic materials having various acoustic properties and interfaces, and various numbers of individual layers may be measured with exemplary embodiments of the invention.

What is claimed is:

1. A method for measuring a thickness of a layer in a multilayer article, the multilayer article comprising a plurality of layers separated by interfaces, the method comprising the steps of:

selecting a center frequency of a transducer positioned adjacent to an outer layer such that respective pulse echoes produced at the interfaces between layers of the multilayer article each have a common distinguishing feature with a signal to noise ratio greater than or equal to a predetermined value, and the pulse echoes are resolved in time;

determining a transit time correction factor for each layer of the multilayer article based on an actual transit time measured with the transducer adjacent to said outer layer and an apparent transit time measured with the transducer at an opposite outer layer;

propagating a pulse through the multilayer article to produce pulse echoes at the interfaces between the layers of the multilayer article;

determining a measured transit time of the pulse through each layer based on the pulse echoes at the interfaces of each layer; and calculating a thickness of each layer based on the measured transit time and the transit time correction factor.

2. The method of claim 1, wherein the predetermined value is 2.0.

3. The method of claim 1, wherein the multilayer article comprises a plastic material, and the method further comprises the step of coupling a pulse generated by the transducer into the multilayer article through a polystyrene buffer rod and a glycerin couplant, wherein the buffer rod has a length which is greater than or equal to a thickness of the multilayer article.

4. The method of claim 1, wherein the common distinguishing feature is a maximum point on a first half wave of each of the pulse echoes.

5. The method of claim 1, wherein the step of determining a measured transit time comprises:

calculating a period of a center frequency of the pulse echoes at the interfaces of the layer;

determining reference time points of the leading edges of the pulse echoes at the interfaces of the layer based on the period.

6. An apparatus for measuring a thickness of a layer in a multilayer article, the multilayer article comprising a plurality of layers separated by interfaces, the apparatus comprising:

a transducer positioned adjacent to an outer layer which generates a pulse having a center frequency which produces respective pulse echoes at the interfaces between layers of the multilayer article, wherein each pulse echo has a common distinguishing feature with a signal to noise ratio greater than or equal to a predetermined value, and the pulse echoes are resolved in time;

means for determining a transit time correction factor for each layer of the multilayer article based on an actual transit time measured with the transducer adjacent to said outer layer and an apparent transit time measured with the transducer at an opposite outer layer;

means for determining a measured transit time of a pulse propagated through each layer based on pulse echoes produced at the interfaces of each layer; and means for calculating a thickness of each layer based on the measured travel time and the transit time correction factor.

* * * * *